United States Patent [19]

Schleinzer et al.

[11] Patent Number: 4,946,996

[45] Date of Patent: Aug. 7, 1990

[54] PREPARATION OF AN ALLYL AMINE AND QUATERNARY DIALLYL AMMONIUM COMPOUNDS THEREFROM

[75] Inventors: Matthias Schleinzer, Dorsten; Klaus-Wilhelm Lienert, Hamburg, both of Fed. Rep. of Germany

[73] Assignee: The Dow Chemical Company, Midland, Mich.

[21] Appl. No.: 34,179

[22] PCT Filed: Aug. 8, 1986

[86] PCT No.: PCT/EP86/00473

§ 371 Date: Apr. 3, 1987

§ 102(e) Date: Apr. 3, 1987

[87] PCT Pub. No.: WO87/00831

PCT Pub. Date: Feb. 12, 1987

[30] Foreign Application Priority Data

Aug. 8, 1985 [DE] Fed. Rep. of Germany ....... 3528548

[51] Int. Cl.⁵ ............................................ C07C 85/04
[52] U.S. Cl. ..................................... 564/296; 564/484
[58] Field of Search ....................... 564/296, 484, 478; 540/467, 544, 450, 612; 544/53, 59, 88, 178; 548/146, 206, 215, 240, 579; 546/184

[56] References Cited

U.S. PATENT DOCUMENTS

3,461,163  8/1969  Boothe ................................ 564/296
3,471,561  10/1969  Dadekian et al. .................... 564/296

FOREIGN PATENT DOCUMENTS

664427  5/1964  Belgium .
0099302  1/1984  European Pat. Off. ............ 564/296
50-77308  6/1975  Japan .

OTHER PUBLICATIONS

Turner, *The Design of Organic Syntheses*, Elsevier Scientific Publishing Company, (1976).

*Primary Examiner*—Bruce Gray
*Attorney, Agent, or Firm*—Dragan J. Karadzic

[57] ABSTRACT

An allyl amine compound such as an allyl dialkyl amine is prepared by the reaction of ammonia or a water soluble amine with an allyl halide in the presence of an alkali metal or alkaline earth metal hydroxide or carbonate using a two-phase reaction system comprising water and a water-immiscible organic liquid. The allyl amine product is of an exceptionally high purity and contains relatively small amounts of salts. When the reaction method is employed to prepare an allyl dialkyl amine, the allyl dialkyl amine can effectively be quaternized to prepare a pure diallyl dialkyl ammonium compound at high yields.

6 Claims, No Drawings

PREPARATION OF AN ALLYL AMINE AND QUATERNARY DIALLYL AMMONIUM COMPOUNDS THEREFROM

The present invention relates to a method for preparing an allyl amine compound and to a method for preparing a quaternary, diallyl ammonium compound therefrom.

Quaternary diallyl dialkyl ammonium compounds such as diallyl dimethyl ammonium chloride are monomeric materials which can be polymerized, both homo- and copolymerized, to form polymers useful in a variety of applications. For example, a polymer derived, at least partially, from a diallyl dimethyl ammonium chloride can be employed as a flocculant in waste water treatment, as a wet strength agent or retention and drainage aid in the preparation of paper, as an antistatic additive, an acid-dye receptor or a biocide.

Heretofore, quaternary diallyl dialkyl ammonium compounds have conventionally been prepared, on a commercial scale, by the reaction, in an aqueous medium, of a secondary amine such as dimethyl amine with an allyl halide (e.g., allyl chloride) in the presence of an alkali metal hydroxide (e.g., sodium hydroxide). See, for example, U.S. Pat. No. 2,923,701. In general, an excess of the allyl halide is employed to ensure complete reaction of the secondary amine. The excess allyl halide is stripped under vacuum. The resulting product is an aqueous solution containing the desired quaternary diallyl dialkyl ammonium compound. Unfortunately, a large amount of salt (e.g., sodium chloride) is formed during the reaction, and is present in the reaction product. This restricts the ability to polymerize the resulting compound.

Various methods have been proposed to reduce the amount of salt and otherwise improve the purity of the quaternary ammonium product. See, for example, U.S. Pat. No. 3,472,740. Using the described techniques, the purity of the quaternary ammonium compound is improved while simultaneously reducing the amounts of salt in solution by evaporating water from the aqueous reaction product such as by steam distillation to remove the unreacted allyl chloride and secondary amine and to precipitate the salt. The precipitated salt can subsequently be removed from the aqueous solution by filtration. Following evaporation of the water and removal of the precipitated salt, the aqueous solution of the quaternary ammonium compound can be passed over an activated carbon to further purify the reaction product. Unfortunately, the amounts of water which can be evaporated (and hence, the amounts of salt which can be precipitated from solution) is limited due to the hygroscopic nature of the quaternary ammonium compound. In fact, upon the removal of all possible water, a highly viscous oil of an over-saturated solution of the quaternary ammonium compound in water which still contains a high percentage of salt is formed. Moreover, the described purification method is time consuming and capital intensive.

Yet another means for reducing the amount of salt formed in the preparation of the quaternary ammonium compound is disclosed in Japanese patent specification 50-77308. Specifically, the disclosed method comprises precipitating the salt with organic solvent following the reaction of dialkyl amine with allyl halide. Subsequently, the precipitated salt is removed to yield an aqueous solution of the quaternary ammonium compound. Unfortunately, the described method does not precipitate all the salt and the product still contains a relatively high concentration of salt. Moreover, it is necessary using the described process, to separate the added organic liquid from the mixture of water and quaternary ammonium compound.

In addition to containing relatively large amounts of salt, using the described techniques and other known techniques, the quaternary ammonium compound is prepared as a solution in an aqueous liquid. Therefore, it is necessary to ship large amounts of water in transporting the quaternary ammonium product. In addition, polymerization of the quaternary ammonium compound is limited to aqueous polymerization systems. Moreover, further improvements in yield of the desired quaternary ammonium compound are desired.

The preparation of a solid diallyl dimethyl ammonium chloride has been described in Belgian Patent No. 664,427. The described technique involves a two-step reaction process. In the first reaction step, allyl dimethyl amine is prepared by reacting, in aqueous liquid, dimethyl amine with allyl chloride in the presence of caustic soda. Following this reaction, an additional amount of caustic soda is added to the reaction mixture to separate the allyl dimethyl amine from the remainder of the reaction mixture. Specifically, upon the addition of excess caustic soda, a two-phase system results. The upper phase comprises the desired allyl dimethyl amine and up to and over 10 weight percent water and the lower phase comprises sodium hydroxide, sodium chloride, the remainder of the water, up to and exceeding 5 percent dimethyl amine and small amounts of allyl dimethyl amine. Subsequently, the upper phase is separated from the reaction mixture and dried over caustic soda pellets. The resulting material is distilled and the fraction boiling at 59° to 62° C. collected. This fraction is then added, with freshly distilled allyl chloride, to freshly distilled acetone and reacted to form diallyl dimethyl ammonium chloride in the form of crystals. Although the resulting solid diallyl dimethyl ammonium chloride is relatively pure as compared to a similar product prepared in an aqueous solution using the one step reaction method of the prior art, the yield of dimethyl allyl amine in the first reaction step is only 67.5 percent based on the amount of allyl chloride added. In addition, the water phase contains significant amounts of the allyl dimethyl amine following the first reaction step. Moreover, due to the fact that large amounts of water are present in the allyl dimethyl amine formed during the first reaction step, the problems associated with water removal remain. Hence, the allyl dimethyl amine prepared in the first reaction step, it must be dried over caustic soda pellets to remove the water, a time consuming step.

In view of the stated deficiencies of the prior art methods, it remains highly desirable to provide a method for preparing, at a high yield and purity, an allyl amine compound and a quaternary diallyl ammonium compound which method can suitably be employed in preparing the compound as a solid.

Accordingly, in one aspect, the present invention is a method for preparing an organic soluble allyl amine. The reaction method comprises reacting, in a liquid reaction diluent, ammonia or a water soluble amine with allyl halide in the presence of an alkali metal or alkaline earth metal hydroxide or carbonate and is characterized by the fact that the reaction diluent comprises a two phase liquid system consisting of water and water-immiscible organic liquid.

By preparing the allyl amine in a two-phase liquid system comprising water and a water-immiscible organic liquid, the disadvantages inherent in the prior art processes are eliminated. Specifically, the allyl amine compound will remain, following its preparation, in the organic liquid phase. Alternatively, any salt as well as other impurities formed during the reaction will remain in the aqueous liquid phase. Moreover, the organic liquid phase is essentially water-free or contains relatively low amounts of water. Therefore, the resulting allyl amine does not require purification prior to its subsequent use. The allyl amine compound is useful in the preparation of quaternary ammonium compounds, particularly quaternary, diallyl dialkyl ammonium compounds.

In a second aspect, the present invention is a method for preparing a diallyl dialkyl quaternary ammonium compound by sequentially reacting a secondary amine with allyl halide in a liquid reaction diluent and the presence of an alkali metal or alkaline earth metal hydroxide or carbonate and subsequently reacting the thus prepared allyl dialkyl amine with additional amounts of an allyl halide in a liquid reaction diluent to form a quaternary diallyl dialkyl ammonium salt, said method being characterized by the fact that the reaction of the secondary amine and allyl halide is conducted in a two-phase reaction system comprising an aqueous liquid and a water-immiscible organic solvent and at least a portion of the organic liquid phase is separated for further reaction of the allyl dialkyl amine contained by this organic phase to prepare the diallyl dialkyl quaternary ammonium compound.

Using the described two-step method, following the first reaction step in which the allyl dialkyl amine is prepared, the organic phase contains the allyl dialkyl amine and essentially no salt or water. Therefore, this phase can be separated from the aqueous phase and the allyl dialkyl amine directly (i.e., without purification) reacted with additional amounts of the allyl halide to form the quaternary, diallyl dialkyl ammonium compound. The quaternary diallyl dialkyl quaternary ammonium formed is a solid material containing no significant amounts of inorganic salt and surprisingly low amounts of other impurities. Therefore, it can readily be polymerized, both homo- and copolymerized, to form a high molecular weight polymer useful in a wide variety of end-use applications.

In the practice of the present invention, the allyl amine compound is prepared from ammonia or an amine represented by the general structural formula:

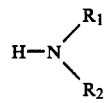

wherein $R_1$ is hydrogen, an alkyl group, or a hydroxy alkyl group and $R_2$ is an alkyl or hydroxy alkyl group. Alternatively, the combination of $R_1$ and $R_2$ can form a cyclic ring such as represented by the following general formula:

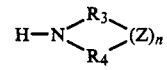

wherein each $R_3$ and $R_4$ are individually $(CR_5H)_p-(CR_6H)_q$ and each $R_5$ and $R_6$ are independently hydrogen or an alkyl group (preferably methyl, ethyl or propyl), p is an integer from 0 to 4 (preferably 1 or 2), q is an integer from 0 to 4 (preferably 1 or 2), the sum of p and q is 1 to 4, Z is oxygen or sulfur and n is 0 or 1. $R_1$ is advantageously hydrogen or an alkyl or hydroxyalkyl group and $R_2$ is an alkyl or hydroxyalkyl group. Preferably, the amine is a secondary amine wherein each $R_1$ and $R_2$ is independently an alkyl group having from 1 to 12 carbon atoms or a hydroxyalkyl group having from 2 to 8 carbon atoms. More preferably, the amine is a secondary amine wherein each $R_1$ and $R_2$ is individually methyl, ethyl or hydroxy ethyl. Most preferably, each $R_1$ and $R_2$ is independently methyl or ethyl.

The allyl halides employed in the practice of the present invention are advantageously allyl halide, methallyl halide or ethallyl halide with the halide preferably being chloride or bromide, most preferably chloride. Most preferably, allyl chloride is employed in the practice of the present invention.

The allyl amines are prepared by reacting ammonia or an amine with the allyl halide in the presence of an alkali metal or an alkaline earth metal hydroxide or carbonate. Of these compounds, those advantageously employed are the alkali metal hydroxides or carbonates with the alkali metal hydroxides being preferred. Potassium hydroxide or sodium hydroxide, particularly sodium hydroxide are most preferred.

The amounts of the amine, allyl halide and hydroxide or carbonate most advantageously employed in preparing the allyl amines are dependent on a variety of factors including the specific reactants employed and the conditions of reaction and can readily be determined by those skilled in the art by simple experimentation. In general, the allyl amine is prepared using from 0.9 to 3 equivalents of amine for each equivalent of allyl halide. It is generally preferable to use a stoichiometric excess of amine, with from more than 1 to 2.5 equivalents of amine preferably being employed for each equivalent of allyl halide. The hydroxide or carbonate is advantageously employed in an amount sufficient to completely neutralize the hydrochloric acid formed by the reaction of the allyl halide with amine, but large amounts of the hydroxide or carbonate are generally not preferred. When employing the preferred alkali metal hydroxide, the hydroxide is advantageously employed in an amount from 0.9 to 5 moles per mole of the allyl halide.

In a preferred embodiment of this invention wherein the allyl amine is prepared by reacting a secondary amine and an allyl halide in the presence of an alkali metal hydroxide, the molar ratio of the secondary amine:allyl halide:alkali metal hydroxide is advantageously 1:0.5–1.2:0.98–2, with molar ratios of 1:0.8–1.05:1.0–1.1 being preferred.

In the practice of the present invention, the allyl halide, amine and hydroxide or carbonate are mixed in a two-phase reaction system comprising water and a water-immiscible organic liquid and reacted at conditions sufficient to form the desired allyl dialkyl amine. By the term "water-immiscible organic liquid", it is meant an organic liquid which, at the reaction conditions employed, cannot uniformly be mixed or blended with water to form a single liquid phase. Preferably, less than 5 weight percent water is capable of being dissolved in the specific organic liquid employed at 20° C. and 760 mmHg. Preferably, at 20° C. and 760 mmHg, the organic liquid contains less than 1, more preferably less than 0.5, most preferably less than 0.25 weight percent of dissolved water.

Representative organic liquids which are suitably employed in the practice of the present invention include aromatic hydrocarbons such as toluene, benzene, m-, o-, and p-xylenes, mesitylene, ethylbenzene and cumene; chlorinated hydrocarbons such as trichloroethylene, tetrachlorocarbon, methylene chloride and perchloroethylene; aliphatic hydrocarbons having 6 or more carbon atoms such as hexane, heptane, cyclohexane; petroleum ethers; and lower dialkyl ethers such as diethylether, diisopropyl ether or ethyl propyl ether. Compatible mixtures of two or more of the specified organic liquids can be employed.

Preferably, the organic liquid employed is an aromatic hydrocarbon, particularly benzene or toluene and various chlorinated hydrocarbons, particularly trichloroethylene. More preferably, the organic liquid is an aromatic hydrocarbon, with toluene and benzene, particularly toluene, being most preferred.

The term "water" is meant to include tap water, deionized water or aqueous solutions.

The amounts of water and the organic liquid most advantageously employed in the practice of the present invention are dependent on various factors, including the specific organic liquid and reactants, particularly the amine and hydroxide or carbonate, employed and the conditions at which the reaction is conducted. Although not absolutely necessary, water is generally advantageously employed in an amount sufficient to dissolve the entire amounts of salt prepared during reaction as well as the amine and hydroxide or carbonate employed. In general, however, large excesses of water are to be avoided. Preferably, the reaction mixture will contain from 40 to 250 weight percent water based on the total weight of the amine and hydroxide or carbonate employed. The amounts of organic liquid employed are not narrowly critical to the practice of the present invention provided sufficient amounts are employed to dissolve the allyl amine product. The organic liquid can be employed in amounts from 10 to 1000 or more volume percent based on the total volume of allyl halide employed. However, it is generally preferable, for purposes of economics, to employ the organic liquid in an amount such that the organic phase will contain from 30 to 60 percent, by weight, of the allyl amine reaction product.

Although the relative concentration of the aqueous liquid phase to organic liquid phase is not particularly critical to the practice of the present invention, in general, the volume ratio of organic phase:aqueous phase is advantageously from as low as 0.05:1 to as high as 25:1. The ratio of the volume of organic phase:aqueous phase is preferably from 0.1:1 to 10:1, with a volume ratio of from 0.5:1 to 2:1 being more preferred.

The method of the present invention will now be described with particular reference to the preparation of an allyl dialkyl amine by reacting a secondary amine with an allyl halide in the presence of an alkali metal hydroxide. However, it is easily extended to include the production of other allyl amines using different amines, allyl halides and hydroxides or carbonates.

In preparing the allyl dialkyl amine, the alkyl halide and alkali metal hydroxide are preferably added, in a controlled manner over a period of time, to a mixture of the water, organic liquid and secondary amine. By the controlled addition of the allyl halide and alkali metal hydroxide, the secondary amine is present at high concentrations, in comparison to the concentration of the allyl halide and alkali metal hydroxide, which suppresses the formation of a water-soluble diallyl dialkyl ammonium salt as well as by-products related thereto reduced.

The temperatures most advantageously employed in reacting the allyl halide with the secondary amine are dependent on the specific reactants employed, the type and concentration of the organic liquid employed, the relative ratio of the organic phase to the aqueous phase and the desired yields and product properties. In general, the maximum temperature employed is limited by the formation of excessive by-products which tend to color the reaction product whereas the lower temperatures of reaction are limited by the desired rate of reaction. In general, the reaction is conducted at a temperature from 15° to 70° C., with temperatures from 20° to 60° C. being more preferred. The reaction mixture is advantageously maintained at these temperatures for a period of from 2 to 10 hours, more preferably from 5 to 9 hours.

During the addition of the alkali metal hydroxide and allyl halide to the reaction mixture and subsequent reaction of the secondary amine with the allyl halide, the reaction mixture is advantageously agitated.

Upon completion of the reaction, the thus prepared allyl amine compound is contained in the organic phase (i.e., is dissolved in the organic liquid). In addition to the desired reaction product, the organic phase may contain small amounts of unreacted secondary amine and allyl halide. Alternatively, the aqueous phase will contain alkali metal halide (e.g., sodium chloride) unreacted secondary amine and impurities. The organic and aqueous phases are then separated and the thus prepared allyl amine compound can be used without subsequent purification.

In a preferred embodiment of the present invention, the allyl amine compound which is prepared is an allyl dialkyl amine and this reaction product is quaternized to form a quaternary ammonium compound. In conducting the quaternization reaction, the allyl dialkyl amine and allyl halide are advantageously mixed in a liquid reaction diluent at conditions sufficient to quaternize the allyl dialkyl amine. In one method for preparing the quaternary, diallyl dialkyl ammonium compound from the allyl dialkyl amine, quaternization can be conducted by adding allyl halide directly to the separated organic phase containing the allyl dialkyl amine. Alternatively, the allyl dialkyl amine product can be recovered at an exceptional purity from the separated organic liquid phase and, following separation, the allyl dialkyl amine redissolved in the same or different liquid for subsequent quaternization to the desired diallyl dialkyl ammonium compound.

Preferably, the quaternary ammonium compound being prepared is insoluble in the liquid employed as the reaction diluent in the quaternization reaction. Specifically, although various polar solvents such as dimethyl sulfoxide, dimethyl formamide, acetonitrile, water or a mixture of water and a water-immiscible organic liquid can be employed as the reaction diluent for the quaternization reaction, the resulting quaternary ammonium compound is generally soluble in these liquids making recovery of the product, in the solid form, difficult. Advantageously, the quaternization of the allyl dialkyl amine to a diallyl dialkyl ammonium compound is conducted in an essentially water-free reaction medium due to the fact that the presence of water in the quaternization reaction mixture will result in the formation of some oily, non-crystalline material.

The organic liquids which can be employed in preparing the allyl dialkyl amine can also generally be employed in the quaternization reaction. In addition, other organic liquids which do not possess the necessary immiscibility in water which is required for the preparation of the allyl dialkyl amine using the method of the present invention are also suitably employed as the reaction diluent in the quaternization step. For example, in addition to those organic liquids which can be employed in preparing the allyl dialkyl amine, lower ketones such as acetone, methyl ethyl ketone and acetophenone can advantageously be employed as the reaction diluent in the quaternization reaction. The preferred organic liquid for use as the quaternization reaction diluent include the lower ketones, particularly acetone; the aromatic hydrocarbons and chlorinated hydrocarbons. Most preferably, quaternization is conducted in a lower ketone, with acetone being most preferred.

The rate of the quaternization reaction as well as the nature and purity of the quaternary ammonium compound prepared during the quaternization are influenced by the amounts and specific reactants and organic liquid reaction diluent employed. In general, to obtain a product of desired purity, the organic liquid reaction diluent is advantageously employed such that the reaction mixture advantageously contains at least two volumes of the organic liquid for each volume of the allyl dialkyl amine to be quaternized. Preferably, from 2 to 50 volumes of the organic liquid reaction diluent are employed for each volume of the amine to be quaternized. More preferably, from 2 to 5 volumes of the organic liquid reaction diluent are employed for each volume of the allyl dialkyl amine.

The allyl halide is employed in at least a stoichiometric amount. Preferably, to avoid significantly long reaction times, the allyl halide is employed in an amount of at least 1.5 moles for each mole of the allyl dialkyl amine to be quaternized. More preferably, from 1.5 to 6, most preferably from 2 to 3, moles of the allyl halide are employed for each mole of the allyl dialkyl amine to be quaternized.

Using these amounts of allyl halide, the quaternization reaction is advantageously conducted at temperatures from 20° to 60° C., preferably from 30° to 45° C. At these temperatures, the quaternization reaction is generally conducted for periods of from 6 to 15 hours.

Using a sufficiently non-polar solvent, following the quaternization of the allyl dialkyl amine, the resulting quaternary diallyl dialkyl ammonium compound will precipitate from solution. The quaternary ammonium compound can therefore be recovered using conventional filtration techniques. Prior to subsequent use, the filtered product is then dried to form a solid, quaternary diallyl dialkyl ammonium compound. The resulting solid crystal, although containing traces of the organic solvent, is of relatively high purity and contains essentially no alkali metal halide. Therefore, it can easily be polymerized to high molecular weights in both aqueous and non-aqueous systems. Since the resulting polymer contains no salt, it can be employed in a wide variety of applications to which polymers containing higher concentrations of salt cannot be employed.

The following examples are set forth to illustrate this invention and should not be construed to limit its scope. All percentages and parts in the examples are by weight unless otherwise indicated.

EXAMPLE 1

A. Preparation of an Allyl Dimethyl Amine

To a suitably sized flask equipped with a thermometer, agitator, reflux condensor operating at a temperature of −45° C. and heating and cooling means was added 1240 milliliters (ml) of a 40 percent aqueous solution of dimethyl amine and 1000 ml parts cf toluene. During this addition, the temperature of the vessel was maintained at 25° C. While agitating the dimethyl amine/water/toluene mixture, a first stream of a solution of 41 grams. (gm) of sodium hydroxide, 60 ml of water and a second stream of 820 ml of allyl chloride were simultaneously added dropwise to the flask over a period of 5 hours. Following complete addition of the sodium hydroxide and allyl chloride, the reaction mixture comprised a molar ratio of dimethyl amine:allyl chloride:sodium hydroxide of 1:1:1.05. During the addition of the allyl chloride and sodium hydroxide, the temperature of the reaction mixture rose. It was maintained at 40° C. during the addition and subsequently slowly increased to 70° C. At this temperature, the reaction mixture was maintained under a slight reflux. The temperature was maintained at 70° C. for 3 hours (total reaction time was 8 hours) after complete addition of the allyl chloride and sodium hydroxide. The reaction mixture was then cooled to 25° C. and agitation stopped. Upon ceasing agitation, the toluene phase which contained allyl dimethyl amine rose to the top of the reaction vessel and the aqueous phase which contained the sodium chloride salt sank to the bottom of the reaction vessel. The toluene phase was separated from the aqueous phase of the reaction vessel. Upon analysis of the organic phase, it was found that the yield of allyl dimethyl amine was over 90 percent based on the amounts of allyl chloride employed.

B. Quaternization in Toluene

The thus prepared allyl dimethyl amine was quaternized without subsequent separation or purification by deleting a portion of the resulting solution of allyl dimethyl amine with additional toluene to form a 35 percent solution. One hundred grams of this solution were placed in a suitable reaction vessel and 200 ml of allyl chloride added thereto at room temperature. The resulting mixture was heated to a temperature of 35° C. for a period of 8 hours. At this time, the diallyl dimethyl ammonium chloride product (with essentially complete conversion) had precipitated from solution and was filtered, washed with water-free toluene and dried under vacuum. The resulting solid crystals of the diallyl dimethyl ammonium chloride were extremely pure, containing essentially no (i.e., less than 100 parts of sodium chloride per million parts (ppm) of the quaternary ammonium compound) sodium chloride and could effectively be employed for subsequent polymerization.

C. Quaternization in Acetone/Toluene

A second portion of the allyl dimethyl amine was quaternized by adding 150 gm of the solution of the allyl dimethyl amine in toluene to 500 ml acetone containing 58 ml of allyl chloride. The solution was heated to a temperature of 40° C. for a period of 24 hours. The diallyl dimethyl ammonium chloride formed by the quaternization reaction precipitated from solution in long, uncolored needles. Conversion was greater than 95 percent. The needles were recovered using conventional filtration techniques and dried under vacuum. The filtered needles were found to be pure and to contain essentially no sodium chloride and could subsequently effectively polymerize.

When the same quaternization was repeated except using reaction temperatures of 25° C., a product of similar purity was prepared except that the quaternization reaction required two days.

D. Quaternization in Acetone

A third portion of the toluene solution containing the allyl dimethyl amine was fractionated. The fraction boiling at 61° to 63° C. was collected. Sixty grams of this fraction were added to 136 gm acetone containing 156 gm of allyl chloride. The mixture was maintained at a temperature of 35° C. for a period of 8 hours at which time there was greater than 95 percent conversion. The quaternary ammonium compound precipitated in long, uncolored needles from solution. The needles were recovered using conventional filtration techniques and found to be of an extremely high purity. Specifically, the diallyl dimethyl ammonium chloride product contained less than 2 ppm acetone, less than 0.7 ppm dimethyl amine, less than 0.4 ppm of unreacted allyl dimethyl amine, 20 ppm of allyl dimethyl amine.HCl and less than 40 ppm of sodium chloride. Comparatively, the diallyl dimethyl ammonium chloride prepared by the methods of the prior art contain at least 1 percent (10,000 ppm) sodium chloride.

E. Quaternization in Trichloroethylene

Another portion of the allyl dimethyl amine was fractionated and the fraction of the product boiling at 61° to 63° C. recovered. One hundred grams of the resulting fraction were added to 500 gm of trichloroethylene. Subsequently, 270 gm of allylchloride were added to the mixture. The temperature of the reaction mixture was maintained at 35° C. for 8 hours. The reaction mixture was continuously agitated during addition of allylchloride and thereafter. At this time, needles of dimethyl dialkyl ammonium chloride floated in a thick layer on the surface of the solution. The needles were filtered and dried using conventional techniques. They are of extremely high purity and contain less than 4 ppm trichloroethylene, less than 60 ppm of amines and less than 40 ppm sodium chloride.

F. Quaternization in the presence of Water

Yet another portion of the toluene solution of allyl dimethyl amine was quaternized by placing 150 gm of the allyl dimethyl amine solution and 17.1 ml of allyl chloride in 200 ml water. The resulting mixture formed a two-phase system, i.e., a toluene phase containing the allyl dimethyl amine and allyl chloride and an aqueous phase. The two-phase system was agitated and the temperature increased to 40° C. This temperature was maintained for 8 hours, at which time essentially complete conversion of the allyl dimethyl amine to diallyl dimethyl ammonium chloride had taken place. The diallyl dimethyl ammonium chloride was contained in the aqueous phase. The toluene phase which contained the excess allyl chloride was separated from the aqueous phase which contained, in solution, the diallyl dimethyl ammonium chloride. To remove any remaining toluene and volatile impurities from the aqueous phase, it was subjected to a stripping operation for three hours at 40° C. and a pressure of 150 mmHg. Following the stripping operation, the aqueous solution comprised 60 percent, by weight, of the diallyl dimethyl ammonium chloride and essentially no sodium chloride. The resulting diallyl dimethyl ammonium chloride was effectively polymerized using conventional techniques.

G. Quaternization in a Highly Polar Solvent

Another portion of the allyl dimethyl amine in toluene was fractioned and the fraction boiling at 61° to 63° C. collected. Sixty grams of this fraction were dissolved in 100 gm of dimethyl sulfoxide containing 57 ml of allyl chloride. The temperature of the resulting mixture was increased to 60° C. It was maintained at this temperature, with agitation, for a period of 8 hours at which time the allyl dimethyl amine was essentially completely converted to diallyl dimethyl ammonium chloride. The diallyl dimethyl ammonium chloride product was soluble in the dimethyl sulfoxide. It could effectively be polymerized in the organic solution using conventional techniques.

EXAMPLE 2

Into a suitably sized reaction vessel equipped with reflux means (maintained at −45° C.), addition funnels, stirrer, heating and cooling means and thermometer was added 1836 ml of a 40 weight percent solution of dimethyl amine in water and 200 ml toluene. During this addition, the reaction vessel was maintained at 25° C. Subsequently, 682 ml of 50 weight percent aqueous solution of sodium hydroxide was added dropwise to the dimethyl amine/water/toluene mixture over a period of three hours. Simultaneous with the addition of the sodium hydroxide was added 1077 ml of allyl chloride. During the addition of sodium hydroxide and allyl chloride, the reaction mixture was maintained at a temperature of 25° C. Following complete addition of allyl chloride and sodium hydroxide, the molar ratio of dimethyl amine:allyl chloride:sodium hydroxide contained in the reaction vessel was 1.115:1:1. After complete addition of sodium hydroxide and allyl chloride, the temperature of the reaction mixture was slowly increased to 55° C. This temperature was maintained for an additional three hours. The flask was then cooled to 20° C. At this time, the toluene phase which contained the allyl dimethyl amine reaction product formed a top layer whereas the aqueous phase which contained the sodium chloride formed a bottom layer. The yield, based on the amounts of allyl chloride fed to the reactor, was over 80 percent. The allyl dimethyl amine product can be quaternized using any of the foregoing techniques in Example 1 (B-G) to form diallyl dimethyl ammonium chloride, as a solid or an aqueous or organic liquid solution, at a surprisingly high purity.

EXAMPLE 3

To a suitably sized and equipped reaction vessel containing 200 gm of n-hexane was added 200 gm of a 50 weight percent aqueous solution of morpholine. The resulting mixture was vigorously agitated. Subsequently, 82 gm of allyl chloride was added dropwise to the reaction mixture over a 3 hour period. Simultaneously, 82 gm of a 50 weight percent solution of sodium hydroxide in water were added within 3 hours. During this addition, the temperature was maintained at 30° C. The vessel was heated to 60° C. for an additional 5 hours, then cooled to room temperature. The organic phase was separated and fractionated. The fraction boiling at 30 mm Hg and 60° C. contains pure N-allyl morpholine, which can be quaternized using conventional techniques.

We claim:

1. A method for preparing a solid quaternary diallyl dialkyl ammonium compound by sequentially reacting a secondary amine with an allyl halide in a liquid reaction diluent and the presence of an alkali metal or alkaline earth metal hydroxide or carbonate and subsequently reacting the thus prepared allyl dialkyl amine with additional amounts of an allyl halide in a liquid reaction diluent to from a quaternary diallyl dialkyl ammonium salt wherein the reaction of the secondary amine and allyl halide is conducted in a two-phase liquid reaction diluent comprising an aqueous liquid and a water-immiscible organic solvent and at least a portion of the organic liquid phase is separated for further reaction of the allyl dialkyl amine contained by this organic phase to prepare the quaternary diallyl dialkyl ammonium compound in an organic liquid quaternization reaction diluent.

2. The method of claim 1 wherein said allyl halide is added directly to the separated organic phase to quaternize the allyl dialkyl amine.

3. The method of claim 1 wherein said allyl dialkyl amine is recovered from the separated organic liquid phase and redissolved in the same or different organic liquid quaternization reaction diluent for subsequent quaternization to the diallyl dialkyl ammonium compound.

4. The method of claim 3 wherein said organic liquid quaternization reaction diluent is an aromatic hydrocarbon, al aliphatic hydrocarbon having six or more carbon atoms, a lower ketone or a compatible mixture thereof and from 2 to 50 volumes of the organic liquid are employed for each volume of the amine to be quaternized.

5. The method of claim 4 wherein said organic liquid quaternization reaction diluent is a lower ketone or an aromatic hydrocarbon, the allyl halide is allyl chloride and is employed in at least a stoichiometric amount based on the amount of allyl dialkyl amine to be quaternization reaction is conducted at a temperature from 20° to 60° C.

6. The method of claim 5 wherein said organic liquid quaternization reaction diluent is acetone.

* * * * *